United States Patent [19]

Gwathmey et al.

[11] Patent Number: 4,979,954
[45] Date of Patent: Dec. 25, 1990

[54] STAPLE SUTURING METHOD

[75] Inventors: Owen M. Gwathmey, The Meadow, Box 96, Aylett, Va. 23009; Thomas E. Sloane, Jr., West Redding, Conn.; Robert R. Oddsen, Centerport, N.Y.

[73] Assignee: Owen Gwathmey, Aylett, Va.

[21] Appl. No.: 429,808

[22] Filed: Oct. 31, 1989

Related U.S. Application Data

[60] Division of Ser. No. 307,116, Feb. 7, 1989, which is a division of Ser. No. 18,662, Feb. 25, 1987, Pat. No. 4,809,695, which is a continuation-in-part of Ser. No. 313,514, Oct. 21, 1981, abandoned, which is a continuation-in-part of Ser. No. 175,787, Aug. 6, 1980, abandoned.

[51] Int. Cl.$^5$ .............................................. A61B 17/00
[52] U.S. Cl. ........................................ 606/219; 227/19
[58] Field of Search ........................ 606/219; 411/457; 227/175–182, 19

[56] References Cited

U.S. PATENT DOCUMENTS

| | | | |
|---|---|---|---|
| 3,584,347 | 6/1971 | Klenz | 411/457 |
| 4,526,174 | 7/1985 | Froehlich | 606/219 |
| 4,773,420 | 9/1988 | Green | 227/178 |

*Primary Examiner*—Randall L. Green
*Assistant Examiner*—Gary Jackson
*Attorney, Agent, or Firm*—Griffin Branigan & Butler

[57] ABSTRACT

A tissue suturing method involves C-shaped suturing staples (16) embedded in a cartridge (14) formed of a carrier (18) and opposite cartridge jaws (20 and 22). The opposite cartridge jaws are moved linearly along a track in the carrier to bend the C-shaped staples into spiraling overlapping loops by a separate elongated pliers-like clamping tool (12). The cartridge jaws selectively engage the pliers-like tool jaws (90) so that a loaded cartridge can be mounted on the pliers-like tool, the suturing staples mounted therein can be rolled up from their ends to theregy pass through tissues positioned in mouths of the staples, the cartridge can be removed from the pliers-like tool jaws, and a new loaded cartridge can be mounted on the pliers-like tool jaws to repeat this process. An equalizer mechanism (84) is included on the pliers-like tool to cause opposite jaws of the pliers-like tool to move correspondingly uniformed distances.

2 Claims, 4 Drawing Sheets

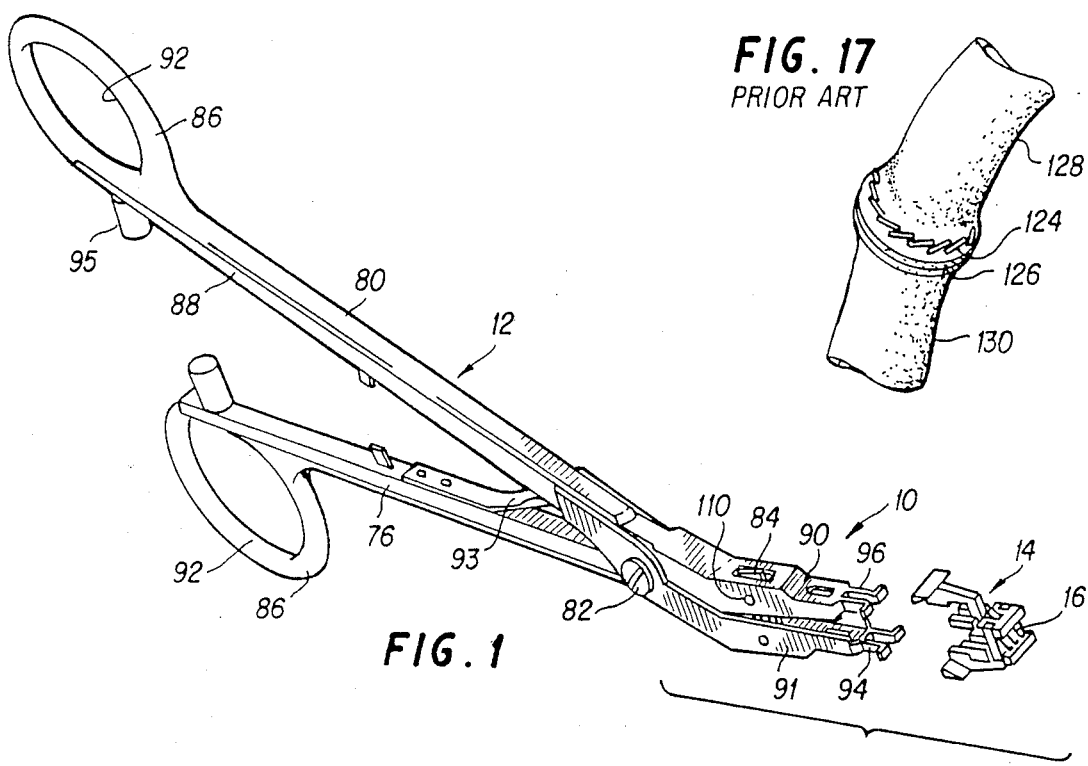
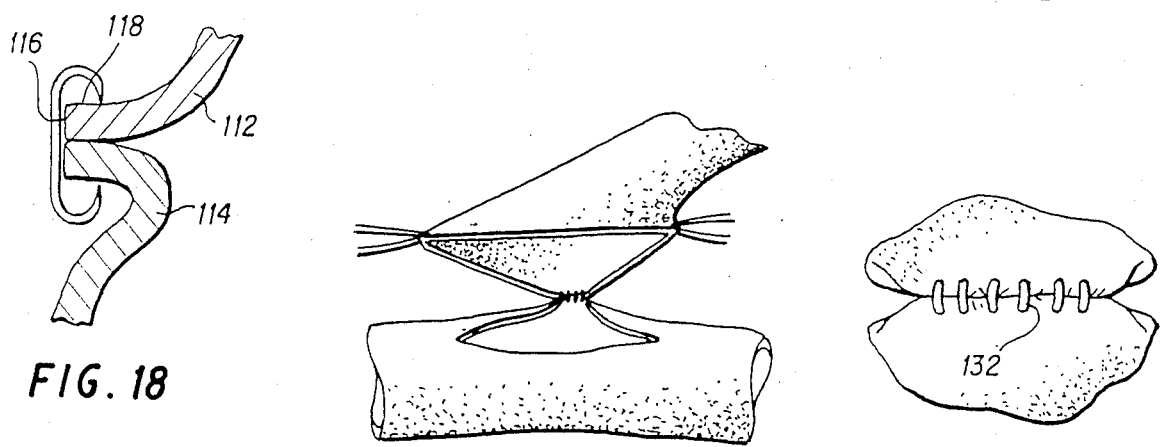
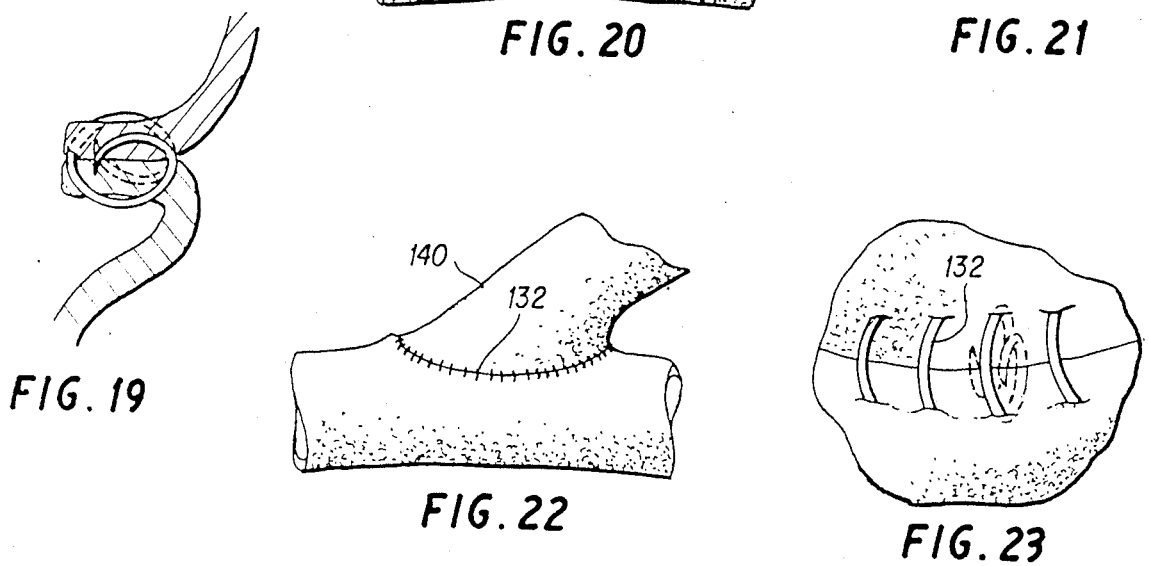

STAPLE SUTURING METHOD

This is a Divisional application of Ser. No. 07/307,116, filed Feb. 7, 1989, which was a divisional application of Ser. No. 07/018,662, filed Feb. 25, 1987, now Pat. No. 4,809,695, which was a continuation-in-part application of Ser. No. 06/313,514, filed Oct. 21, 1981, now abandoned, which was a continuation-in-part application of Ser. No. 06/175,787, filed Aug. 6, 1980, now abandoned.

BACKGROUND OF THE INVENTION

This invention relates generally to the art of surgical suturing, and more particularly to suturing devices and methods which employ surgical staples.

A major time consumer in performing surgery is suturing tissues together. In this regard, when performing heart surgery, implant surgery, and many other types of surgery, surgeons must often anastomos blood vessels to other blood vessels, which procedure is normally performed by laboriously stitching edges of blood-vessel openings together. Because the blood vessels are so small and delicate, this procedure often takes hours to accomplish. The suturing of blood vessels and other organs together often forms a large part of a surgical operation, and this time factor can limit the development of, and use of, certain procedures. It is an object of this invention to provide an assembly and method for suturing tissues together, especially blood vessels and other organs, in a relatively rapid manner, thereby significantly reducing the time required for carrying out complicated surgical procedures.

Many surgical stapling systems have been suggested and, in fact, a few are commercially available. However, such devices are normally too big and cumbersome to be practically used for blood vessel anastomosis. It is therefore another object of this invention to provide a surgical stapling system which is sufficiently delicate in size, shape and opertion that it can be used for blood vessel anastomosis.

It has long been recognized that it is preferable to suture tubular organs such as blood vessels, together with individual, independent, radially-aligned stitches, rather than by using a continuous suturing thread extending circumferentially about the tubular organs. One reason for this is that if a blood vessel, for example, is stitched together with a continuous, circumferential, suture thread and the stitches are pulled tightly during the suturing, it will have a "purse string" effect, which tends to constrict the blood vessel at the point of the suture. This "purse-string" effect is magnified in young patients as the patient and his blood vessels grow, since the continuous suture thread will not allow the vessel's internal size to increase with such growth. Individual, unconnected, radially-aligned stitches placed about blood vessels, on the other hand, will not cause this purse-string effect and will allow blood vessels to grow between the stitches. Another reason individual, radially-aligned, stitches are preferable to circumferential continuous-thread stitches is that the continuous thread stitches tend to restrict blood-flow to isolated tissue positioned radially beyond the suture. In some cases this tissue later dies thereby releasing the suture threads and causing the suture to fail. In spite of these tremendous disadvantages most surgeons still use continuous-thread circumferential stitching for tubular organs because it is much faster than positioning independent, radially aligned stitches about tubular organs. Unfortunately, most prior-art staplers, and/or clamps which have been suggested for tubular organs have the same disadvantages as continous-filament sutures. In this respect, many of these systems involve staples each having a long back section which is positioned circumferentially about a tubular organ and end legs which pass through everted edges of the tubular organ. When the end legs are folded toward the back section to close these staples they squeeze the everted tissue between the staple legs and the back section thereby restricting blood flow across the staples. Often such staples are applied to overlap with one another. Such an arrangement of staples provides a "purse string" effect because the circumferentially positioned back sections do not allow the tubular organs to grow radially and they tend to cut off circulation in isolated everted edges of the tubular organs which are positioned radially outside of the staples. It is therefore an object of this invention to provide a stapling assembly and method which not only reduces the time for suturing but which allows a surgeon to suture tubularly-shaped organs, such as blood vessels, with individual, radially-aligned stitches so as not to constrict the tubularly-shaped organs and not to cut off circulation to portions of everted tissue of the tubularly-shaped organs positioned radially outside of the stitches.

Yet another problem with many staple systems is that each of the staples thereof, when opposite legs thereof are bent against an elongated back section thereof, forms an elongated member. Such a shape sometimes allows tissues of two organs stapled together to slide along the back section of the staple to opposite ends thereof, thereby separating from one another. In other words, the long, rectangular, shape of many prior-art staples, allows two tissues to pull apart, with one tissue moving to one end of the staple, and the other tissue moving to the other end of the staple. Thus, it is an object of this invention to provide a stapling apparatus and method which provides a substantially round staple which cannot, therefore, reorient itself to allow separation of tissues stapled together therewith.

Yet another difficulty with many prior art suturing staple devices is that the staples themselves either allow tissue stapled therewith to work itself loose or they include complicated fastening devices which prevent the opening thereof. It is an object of this invention to provide a stapling apparatus and method having staples which, once they are stapled onto tissue, do not allow the tissue to easily free itself from the staples but which do not involve the use of complicated catches or the like on the staples to hold legs thereof together.

SUMMARY

A suturing staple assembly and method involves the use of a pliers-like tool and removable cartridges having aligned C-shaped staples embedded therein. Each of the cartridges contains one or more C-shaped staples and comprises a carrier having jaw tracks thereon and linearly movable cartridge jaws which ride in these tracks. Plier-tool jaws engage the cartridge jaws to cause them to slide along the track, thereby rolling up the C-shaped staples from their ends into spiralled, overlapping loops. During this rolling process, pointed tips of legs of the C-shaped staples pass through tissue located in the mouths of the C-shaped staples. Also during this rolling process, the staples are withdrawn from their embedded engagement with the cartridges. Thus, a staple-loaded cartridge can be mounted on a pliers-like tool, the tool can be manipulated to close the cartridge jaws and thereby roll the legs of the staples into tissue mounted in the mouths of the staples.

BRIEF DESCRIPTION OF THE DRAWINGS

The foregoing and other objects, features and advantages of the invention will be apparent from the following more particular description of the preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 1 is an exploded isometric view of a tissue-suturing assembly of this invention;

FIG. 17 is an isometric view of two blood vessels which have been anasomosed, end-to-end, with a prior-art stapler;

FIG. 18 is a side sectional view of two pieces of tissue having their edges everted to form a flange which is inserted into the mouth of a staple of the assembly of FIG. 1 before the staple has been closed by the cartridge and pliers-like clamping tool thereof;

FIG. 19 is a view similar to FIG. 18 in which the staple has been closed the cartride and pliers-like tool;

FIG. 20 is a isometric view of two blood vessels being anastomosed, a plurality of staples of the type shown in FIGS. 18 and 19 having already been applied to suture vessel wall edges together;

FIG. 21 is an outside isometric view of an anastomosed seam with six staples of this invention having been applied to form the seam;

FIG. 22 is an isometric view showing two blood vessels anastomosed along a seam by staples of this invention; and, FIG. 23 is an isometric close up view of staples of this invention applied to a seam, with portions of one staple embedded in tissue being shown in phantom.

DESCRIPTION OF PREFERRED EMBODIMENTS

Figure 3:
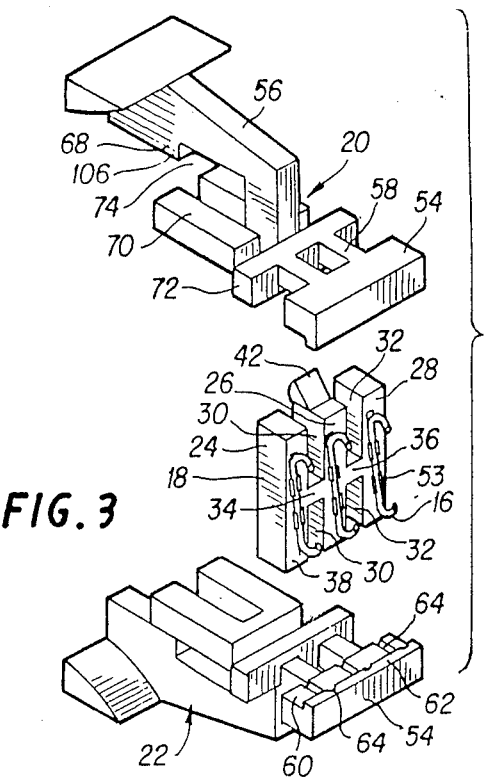
FIG. 3 is an exploded view of the cartridge and staples of FIG. 2.
Figure 4:
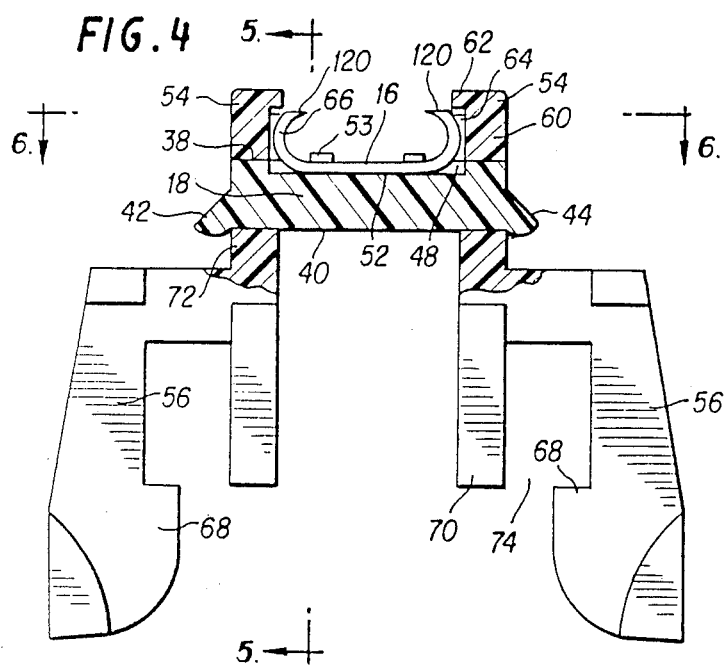
FIG. 4 is a side, partially in section, view of the carriage and staples of FIG. 2.
Figure 6:
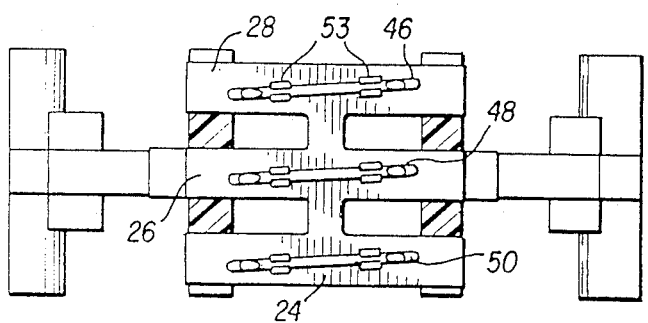
FIG. 6 is a top view taken on line 6—6 in FIG. 4.
Figure 5:
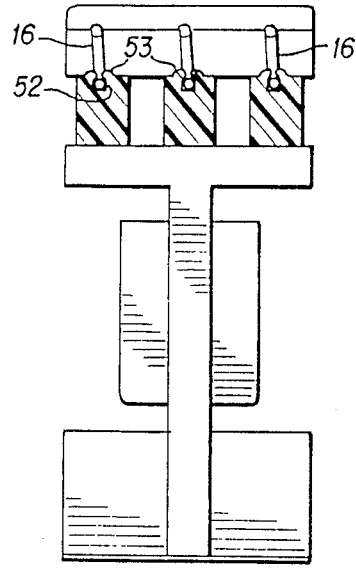
FIG. 5 is a cross sectional view taken on line 5—5 in FIG. 4.

Referring now to the drawings, and particularly to FIG. 1, a tissue suturing assembly 10 of this invention includes a pliers-like clamping tool 12, a plurality of cartridges 14 selectively mountable on the pliers-like clamping tool 12, and a plurality of C-shaped staples 16 being mounted in the cartridges 14. Generally, when a staple-loaded cartridge 14 is mounted on the pliers-like clamping tool 12, the pliers-like clamping tool 12 is manipulated to apply the C-shaped staples 16 onto tissue as will be described below. The pliers-like clamping tool 12 is then manipulated to open the cartridge 14, thereby releasing the applied staples 16 and the unloaded cartridge 14 is removed from the clamping tool 12. A new loaded cartridge is then mounted on the pliers-like clamping tool 12 and a staple or staples therein are applied to tissue. Describing first the cartridge 14, with particular reference to FIGS. 2-6, the cartridge 14 is comprised of a carrier 18 (FIG. 3) for defining a linear track and two opposite cartridge jaws 20 and 22 for moving linearly on the linear track. With regard to the carrier 18, the track thereof includes three parallel rails 24, 26, and 28 defining slots 30 and 32 therebetween and being joined at their middles by cross supports 34 and 36. Each slot 30 and 32 is open toward opposite ends of the carrier 18 but is closed in the middle of the carrier by the cross supports 34 and 36. Generally, each rail 24-28 is rectangular in cross section, having a flat top side 38 and a flat bottom side 40 (FIG. 4). Also, the cross supports 34 and 36 are the same thickness as the rails 24, 26 and 28 so that they form continuous top and bottom sides 38 and 40 with the rails 24-28. However, there are stops 42 and 44 located at opposite ends of the carrier 18 which break the plane of the bottom side 40 as can be seen in FIG. 4. In the top side 38 of each rail is located an elongated indentation, or slot, 46, 48 or 50 whose depth is about the same, or slightly greater, than the thickness of a C-shaped staple 16 so that a back section 52 of a C-shaped staple 16 will fit snugly therein. Although each of the slots 46, 48 and 50 is straight, it is on an angle to the longitudinal axis of its respective rail 24, 26 and 28 as is depicted in FIG. 6. The width of each slot 46, 48 and 50 is about the same as or smaller than the thickness of a C-shaped staple 16 so that a back section 52 of a C-shaped staple 16 is held snugly therein. In this regard, the carrier 18 has integral tabs 53 adjacent the slots 46, 48 and 50 which are pressed over the staple backs 52 to hold them in the slots 46, 48 and 50 but which thereafter deform to allow removal of the staple backs from the slots.

Looking now at the opposite cartridge jaws 20 and 22, it will be understood that these elements are mirror images of one another and it is therefore only necessary to describe one of them. Each cartridge jaw is constructed of one-piece, as can be more clearly seen in FIG. 4, and comprises a jaw gripper 54 and a plier-tool engagement section 56 which are joined by follower posts 58. The follower posts 58 are sized to easily fit into the carrier slots 30 and 32 so that the cartridge jaws 20 and 22 can ride on the rails 24, 26 and 28. In this respect, the cartridge rails 24, 26 and 28 and open areas between the jaw follower posts 58 are appropriately shaped so that there is not only sliding engagement between the cartridge jaws 20 and 22 and the carrier, but so that these members maintain their angular positions relative to one another.

Each jaw gripper 54 comprises a backboard 60 and a molding overhang 62 and both of these members define staple-leg indentations or slots 64 therein which line up with staple legs 66 of staples which are mounted in carrier slots 46, 48 and 50. The staple-leg slots 64 are a width for receiving the staple legs 66.

The pliers-like tool engagement section 56 of each of the cartridge jaws 20 and 22 comprises a resilient catch 68, support 70, and a jaw gripper mount 72. The resilient catch 68 and the support 70 are spaced from one another to form a plier-tool receiving space 74.

Looking now in more detail at the pliers-like clamping tool 12, with particular reference to FIG. 1 and FIGS. 7-10, this tool comprises mainly first and second cross arms 76 and 80, a hinge 82, and a uniform-movement control device 84. With regard to the first and second cross arms 76 and 80, these are depicted in FIG. 1 as each being constructed of a plastic finger grip portion 86 at a handle end thereof and a metal portion 88 which is attached to the plastic finger-grip portion 86 at the handle end thereof and extends to the plier-tool jaw end 90. The plastic finger-grip portions form finger holes 92 which a surgeon grips to manipulate the plier-tool jaws 90. In this respect, when the finger grip portions 86 are urged together, this motion is translated through the hinge 82 to close the plier-tool jaws 90 toward one another. A spring 93 maintains the finger grip portions 86 and the jaws 90 normally separated and stops 94 prevent undue closing motion.

Looking more specifically at the plier-tool jaws 90, each of these is the mirror image of the other, and each comprises L-shaped prongs 94, and 96, with each prong having a main shaft 98 (FIG. 8) and an elbow 100 at its end. The main shafts 98 are sized to fit into the track slots 30 and 32 of the cartridge carrier 18 and the main shaft 98 and the elbows 100 form pressure surfaces 102 (FIG. 2) for impinging on outside surfaces of the cartridge-jaw supports 70, the jaw-gripper mounts 72, the cartridge-jaw follower posts 58, and the cartridge jaw grippers 54. Each plier-tool jaw 90 and 91 has a catch slot 104 therein for receiving the resilient catch 68.

Figure 7:
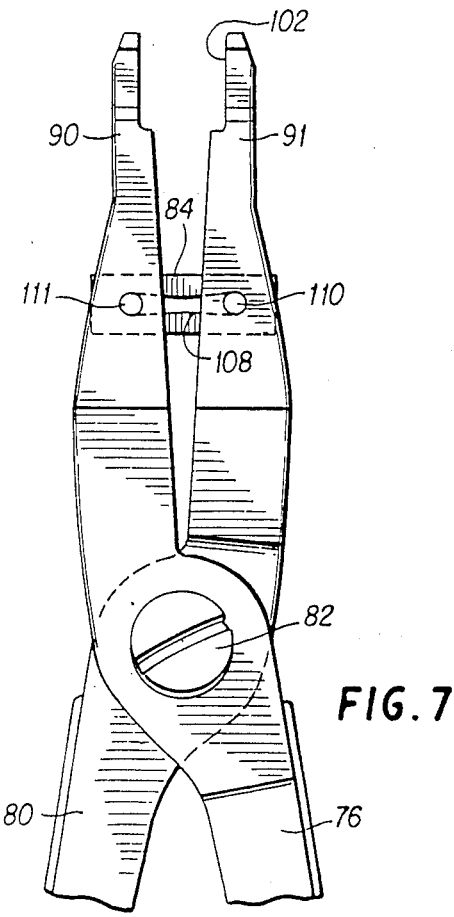
FIG. 7 is an enlarged side view of the jaw end of the elongated pliers-like clamping tool of the tissue-suturing assembly of FIG. 1.
Figure 8:
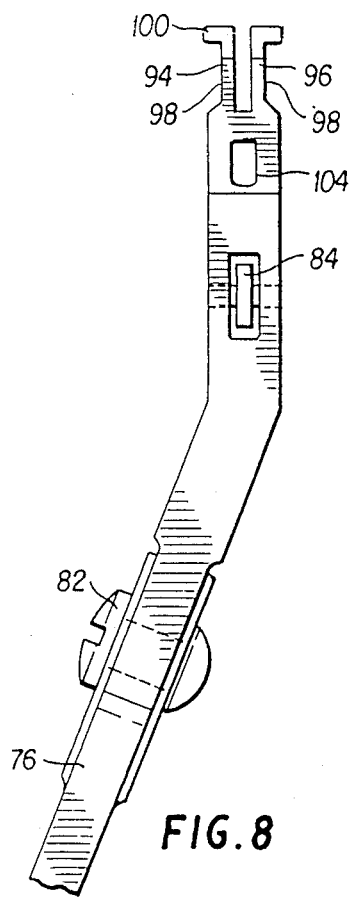
FIG. 8 is an edge view of the structure shown in FIG. 7.

The uniform-unit control device 84 is basically a metallic or plastic spring having an inwardly-converging spring slot 84 therein. A spring-follower pin 110 is mounted on each plier-tool jaw 90 converging spring slot 84 as is depicted in FIG. 7. When a surgeon pushes the plastic finger grip portions 86 of the plier-tool crossed arms 76 and 80 together, the plier-tool jaws 90 and 91 are caused to move uniformly relative to one another by the uniform-movement control device. In this regard, if one spring-follower pin, for example spring-follower pin 110, were to move in the centrally converging slot 84 more than the other, it would tend to open the slot 84 somewhat to allow the other pin to move a comparable amount, and vice versa. This mechanism compensates for the unequal resistance forces that are sometimes encountered by the jaw grippers 54 when they are closed to cause them to move uniformly.

In a preferred embodiment, the cartridge 14 is constructed of a resinous hard plastic such as polycarbonate. The staples 16 are constructed of 316L stainless steel and have diameters ranging from 0.004 inches to 0.1 inch, depending on their uses. As viewed in FIG. 4, the staple legs 66, before a staple is closed, are rounded to a radius r of about 0.060 inches in one embodiment. The staple back section 52, in one embodiment in which the staples are used for blood vessels, is about 0.16 inch long. In this respect, the length of the staple as compared to the radius of the curve of the staple leg 66 should be in the range of 3:1 to 6:1.

Figure 2:
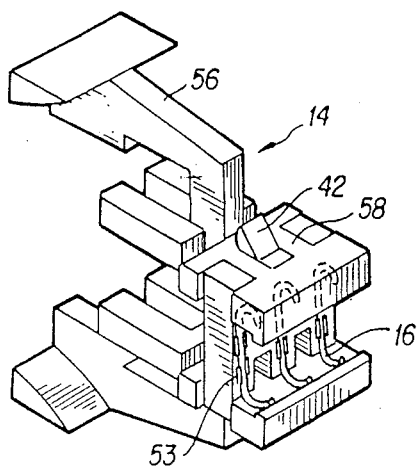
FIG. 2 is an enlarge isometric view of a staple cartridge loaded with three staples for use in the tissue-suturing assembly of FIG. 1.

Describing next the use of the tissue-suturing assembly 10 of this invention, a plurality of cartridges 14 loaded with staples 16 are prepared in a factory. That is, the staple back sections 52 of staples 16 are pressed into carrier slots 48 of carriers 18 and, using heat, ultrasonic energy or other means for heating, the plastic integral tabs 53 are pushed over the back sections 52 of the staples 16 to prevent them from prematurely coming out of the carrier slots 48. Follower posts 58 of carriage jaws 20 and 22 are inserted into the carrier slots 30 and 32 so that the follower posts 58 are inside the carrier stops 42 and so that the staple-leg slots 64 of the jaw grippers 54 align with staple legs 66. Normally the cartridges 14 are assembled before being loaded with staples 16, however, the staples can also be embedded in the carrier slots 48 before the carriage jaws 20 and 22 are mounted on the carrier 18. Thus, a plurality of loaded cartridges as is depicted in FIG. 2 are available. In this respect, although this application depicts cartridges for holding three staples, in the preferred embodiment of this invention there are also cartridges holding one staple, or any number of pluralities of staples. Each cartridge 14 is disposable, that is, it is used only once to apply staples loaded therein and is then discarded. A pliers-like clamping tool 12 is also disposable, being normally used for one opertion with a plurality of loaded cartridges 14 and is then discarded. The pliers-like clamping tool 12 can be packaged with a plurality of loaded cartridges, or can be packaged separately.

Figure 9:
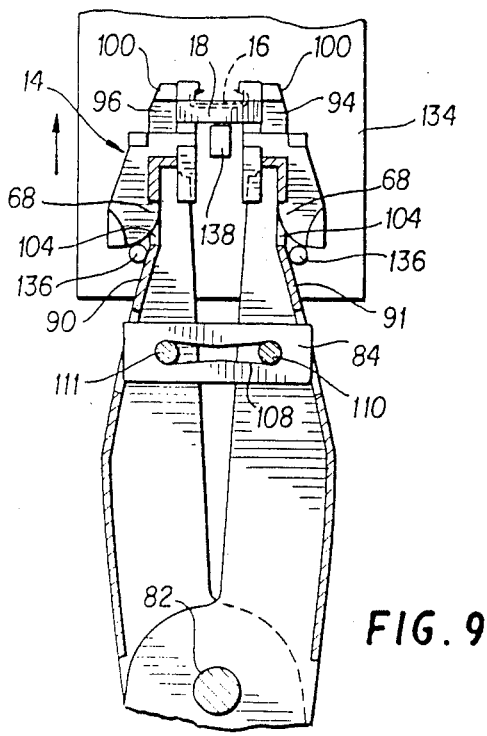
FIG. 9 is an enlarged side sectional view of the jaw end of the pliers-like clamping tool of FIG. 1 with a cartridge having staples therein being mounted thereon, and also showing a cartride removal tool in the background.
Figure 10:
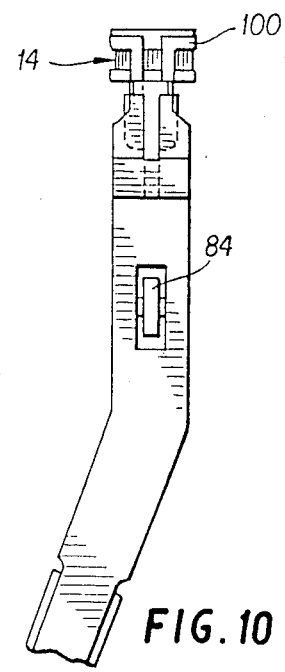
FIG. 10 is an enlarged edge view of the structure of FIG. 9.
Figure 11:
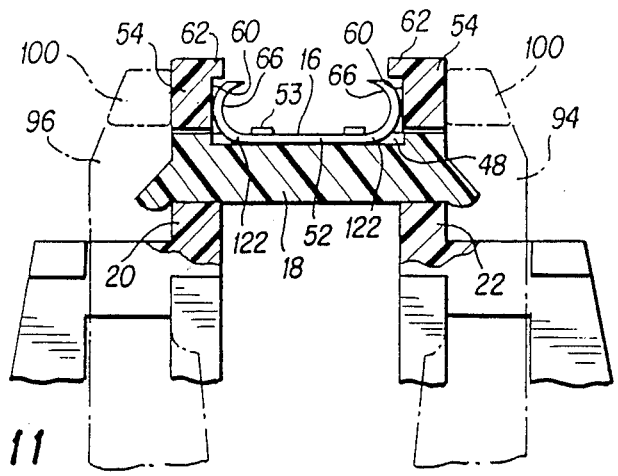
FIG. 11 is a further-enlarged side sectional view of a cartridge with staples therein mounted in the jaws of a pliers-like clamping tool before the pliers-like clamping tool has been manipulated to begin closing the staples.

When a surgeon is prepared to perform an operation using the tissue suturing assembly 10 of this invention, he has a pliers-like clamping tool 12 and a plurality of loaded cartridges 14 available in an operating room. When the surgeon desires to suture a first and second tissue 112 and 114 (FIG. 18) together, he everts their edges slightly and places them together so as to form a flange 118. Such tissues can be the edges of blood vessel walls, as is depicted in FIG. 20. The surgeon inserts the plier-tool jaw prongs 94 and 96 through the plier-tool receiving spaces 74 of a cartridge jaw 20 until the prongs 94 and 96 are positioned as depicted in FIG. 9, with the resilient catch 68 of the jaw engaging the catch slot 104 of the plier-tool jaws 90 and 91. With his finger in the finger holes 92 of the handles, the surgeon then manipulates the loaded, mounted, cartridge 14 to position the everted tissue flange 118 in the mouth of the staples 16. As it can be seen in FIG. 4, pointed tips 120 of the staple legs 66 extend outwardly from the jaw gripper 54. Thus, the surgeon can manipulate the cartridge 14 to dig the staple-leg tips 120 on one side of the cartridge into tissue on one side of the flange 118 while the cartridge is rotated with the pliers-like clamping tool 12 to bring the staple-leg pointed tips on the other side of the cartridge to the other side of the tissue flange so that the staples are in the position shown in FIG. 18 with respect to the tissue flange 118. Thereafter, the surgeon urges the handles of the pliers-like clamping tool 12 together, thereby urging the plier-tool jaws 90 and 91 together. When this is done, the pliers-like jaw prongs 94 and 96 press against the back sides of opposite jaw grippers 54 to urge them toward one another.

Figure 12:
FIG. 12 is an isometric view of one of the staples in the cartridge of FIG. 11.
Figure 13:
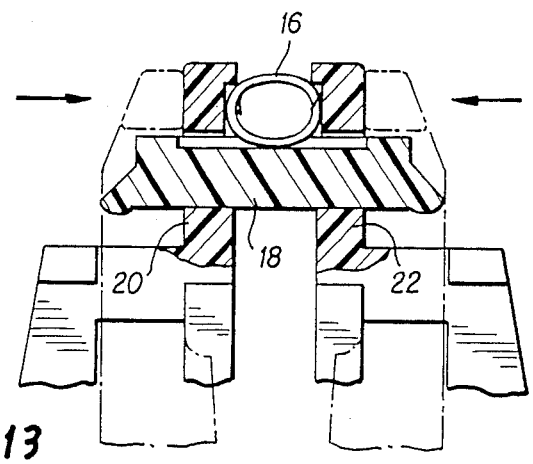
FIG. 13 is a view similar to that of FIG. 11, but with cartridge jaws thereof having been closed to some extent by jaws of a pliers-like clamping tool.
Figure 14:
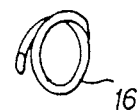
FIG. 14 is an isometric view of one of the staples in the cartridge of FIG. 13.
Figure 15:
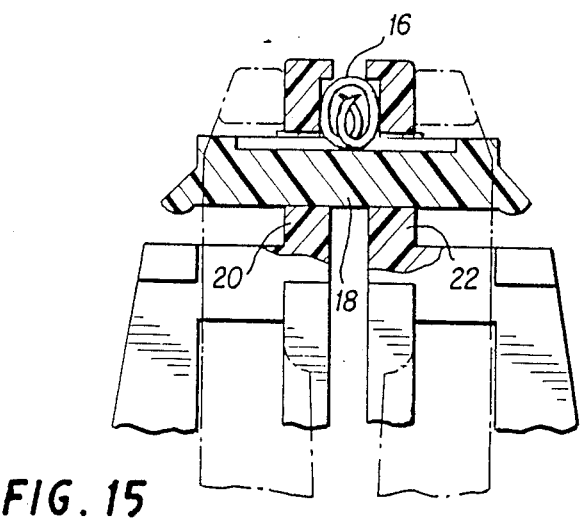
FIG. 15 is a view similar to that of FIGS. 11 and 13, but with the cartridge jaws being closed to a greater extent and the staples therein being rolled up from their ends to a greater extent.
Figure 16:
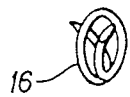
FIG. 16 is an isometric view of a staple mounted in the cartridge of FIG. 15.

As the jaw grippers 54 slide linearly toward one another along the carrier 18 the jaw gripper backboards 60 and the molding overhangs 62 engage the rounded staple legs 66. As the jaw grippers 54 begin moving toward one another, the staples have the appearance as the staple in FIG. 12 with their back sections 52 being held in the carrier slots 48 and thereby prevented from bulging backwardly. Impingement of the molding overhang 62 and the backboard 60 on the staple legs 66 causes the staple legs to slide therealong, thereby bending the staples at the intersections 122 of the staple legs 66 and the staple backs 52 so as to roll up the staple legs from the ends of the staples. As the jaw grippers 54 move progressively inwardly, this point of intersection 122 also moves, with the rounded staple legs 66 rolling into spiral, overlapping loops as is shown in progression in FIGS. 13, 14, 15, and 16. This motion causes the staple back sections 52 to deform the tabs 53, thereby releasing the back sections 52 from the carrier slots 48. Finally two complete spiralled overlapping loops are created as shown in FIGS. 15, 16, 19, and 23. Opposite pointed tips 120 of a staple 16 are prevented from contacting one another by the angles of the carrier slots 46 and these same angles cause the staples to achieve spiralled forms.

Staple sutures formed in this manner have vast improvements over circumferentially oriented, elongated, prior-art staples 124 depicted in FIG. 17. For the circumferentially-oriented prior-art staples 124, an isolated portion 126 of everted tissue which is positioned radially outwardly from the staples 24 is prevented from obtaining a good blood supply through walls of vessels 128 and 130 because these staples 124 squeeze the tissue, thereby forming a tourniquet. The staple sutures 132 of this invention, on the other hand, do not appreciably squeeze the tissue at all, but rather are "rolled" into the tissue. Further, the staple sutures of this invention are radially aligned to a blood vessel 140 (FIG. 22) rather than being circumferential thereof so that there is no isolated tissue positioned outside of the staples which could die from a lack of blood supply. The staple sutures 132 of this invention do not tend to impead the flow of blood nor do they create a "purse string" effect as do the prior art staples 124 depicted in FIG. 17.

Once the surgeon has squeezed the plier-tool handles together to close staples into tissue, he reduces pressure applied with his fingers to allow the spring 93 to open the cartridge jaws 20 and 22. The surgeon then places the pliers-like clamping tool 12, with the empty cartridge 14, on a cartridge removal tool 134 (FIG. 9) having round abuttments 136 and a rectangular abuttment 138 thereon which respectively impinge on the resilient catches 68 and the carrier 18 for disengaging catches 68 and lifting the cartridge 14 from the pliers-like clamping tool 12. Thereafter, a new loaded cartridge 14 is placed on the same pliers-like clamping tool 12 and staples loaded therein are applied to tissue in the manner as described above.

It will be appreciated by those skilled in the art that the tissue suturing assembly of this invention and the method of its use not only considerably reduce the length of time required for many surgical procedures but also provide sutures which have advantages over most staples and continous-filament sutures. Further, the tissue-suturing assembly of this invention combines the easy maneuverability of a pliers-like tool with inexpensive cartridges which can be loaded with staples in a factory.

A further vast improvement of this invention over most prior art staplers is that the staples are rolled into continous spiraled loops without the use of an anvil located on the opposite side of tissue from which the staples are inserted so that the tissue is not unduly squeezed, thereby cutting off blood circulation through the tissue. Also, since the staples are applied by rolling the staple legs to force their end tips outwardly and around, the staple tips are driven outwardly through the tissue, rather than being squeezed onto the tissue so that less tissue eversion is required in order for the staples to grip the tissue. This is a tremendous improvement over prior art staplers with which surgeons must create large overlapping eversions of adjacent tissues before they can staple them together. With this invention the staples tend to go out and grip the tissue to form their own eversions. Although this invention is depicted in FIG. 18 for use with a definite eversion for illustrative purposes, in actual practice such a large, definite eversion is not necessary. In addition to all of these improvements in operation, the spiralled, overlapping looped staples once applied, are extremely secure. The tissues cannot be pulled apart to reorient the staples, or to release from the staples, as with many elongated, rectangular, staples. Further, should the spiralled staples rotate, they will simply continuously rotate into the tissue. However, since the staples in most cases pass through the tissue twice, as is depicted in FIGS. 19 and 23, they tend to stay in one position once they are in place.

It will be understood by those skilled in the art that various changes in form and detail may be made in the tissue-suturing assemblies of this invention without departing from the spirit and scope of the invention. For example, it would be possible to have cartridges loaded with various numbers of staples, and even with a single staple. The tissue-suturing assembly of this invention has been mainly described for use to suture blood vessels, however, it could be used with any tissue in the human body, with perhaps the exception Of bones. It is particularly useful in operations concerning by-pass, replacement, and repair of arteries and veins, however, it can also be used for transplanting tissue or performing grafts. The stapler can be used for joining together any hollow organ or viscus of the body, such as are in the cardiovascular, repiratory, gastro-intestinal, renal, and uro-genital systems. Further, the stapler can by used in patch grafting because of defects in muscular, cardiovascular and other systems.

It would be possible to make a cartride of metal or other materials rather than a plastic material. However, some such other metals might make it more difficult to embed the staples 16 in the carrier 18 with the formable tabs 53.

It will be appreciated by those skilled in the art that the tissue-suturing assembly of this invention, in addition to those benefits already described, reduces the skill requirement of a surgeon for achieving excellent, quick sutures over that which is required for sewing the sutures. Further, staple sutures made with this invention do not create as large an opening in the tissue as do suture needle eyes. Thus, the tissue openings for the staple sutures of this invention are the same size as the staples themselves, whereas for suture threads, the holes are usually bigger to accommodate the eyes of the suture needles.

Still another advantage of this invention is that the pliers-like tool provides an excellent manipulating device for positioning the suturing staples. In addition, this tool gives the surgeon a great deal of "feel" as to how tightly he is placing the suture staples on a tissue. In this manner, the surgeon can close the suture staples to various degrees to accommodate various thicknesses of tissue.

The embodiments of the invention to which an exclusive property or privilege are claimed are defined as follows:

1. A method of closing a C-shaped staple constructed of a bendable material comprising the steps of:
   mounting the C-shaped staple with a central back section thereof being positioned on a carrier having a track formed therein;
   urging opposite legs of said C-shaped staple toward one another by means of linearly moving jaw grippers mounted on said carrier track which impinge on said staple with surface for rolling the ends of said staples together to form a loop.

2. A method of closing a C-shaped staple on tissue to be stapled together, said staple being constructed of a bending material, said method comprising the steps of rolling up ends of the staple so as to form two substantially complete overlapping loops, whereby at least one end tip of the staple passes through the tissue to be stapled together twice.

* * * * *